United States Patent
Dai et al.

(10) Patent No.: US 11,939,630 B2
(45) Date of Patent: Mar. 26, 2024

(54) **FLUORESCENT PCR METHOD FOR DETECTING HLA-B*15:02 ALLELE AND SPECIFIC PRIMER PROBE COMBINATION THEREOF**

(71) Applicant: Shaanxi Lifegen Co., Ltd., Xi'an (CN)

(72) Inventors: Penggao Dai, Xi'an (CN); Zihua Zhong, Xi'an (CN); Hao Wang, Xi'an (CN); Zhiye Cai, Xi'an (CN); Lei Meng, Xi'an (CN); Le Wang, Xi'an (CN)

(73) Assignee: Shaanxi Lifegen Co., Ltd., Xi'an (CN)

( * ) Notice: Subject to any disclaimer, the term of this patent is extended or adjusted under 35 U.S.C. 154(b) by 149 days.

(21) Appl. No.: 17/406,375

(22) Filed: Aug. 19, 2021

(65) Prior Publication Data

US 2022/0177955 A1    Jun. 9, 2022

(30) Foreign Application Priority Data

Dec. 7, 2020   (CN) .......................... 202011431450.8

(51) Int. Cl.
  *C12Q 1/6858* (2018.01)
  *C12Q 1/6881* (2018.01)
(52) U.S. Cl.
  CPC ......... *C12Q 1/6858* (2013.01); *C12Q 1/6881* (2013.01)
(58) Field of Classification Search
  None
  See application file for complete search history.

(56) References Cited

U.S. PATENT DOCUMENTS

2016/0376656 A1* 12/2016 Fang ................. A61K 31/55
                                                       514/217

OTHER PUBLICATIONS

GenBank Accession No. MG886870.1 (*Homo sapiens* MHC class I antigen (HLA-B) gene, HLA-B*15var allele, complete cds, 2018. (Year: 2018).*
Newton (Analysis of any point mutation in DNA. The amplification refractory mutation system (ARMS), Nucleic Acids Research, 17(7): 2503-2516, 1989. (Year: 1989).*
Medrano (Guidelines for the Tetra-Primer ARMS-PCR Technique Development, Mol Biotechnol, 56: 599-608, 2014. (Year: 2014).*

* cited by examiner

*Primary Examiner* — Angela M. Bertagna
*Assistant Examiner* — Carolyn L Greene

(57) ABSTRACT

Disclosed is a fluorescent PCR method for detecting HLA-B*15:02 allele and a specific primer probe combination. In the present disclosure, a set of primers and probes are designed based on an HLA-B*15:02 specific SNP gene locus by using TaqMan probe technology, combining another set of primers and probes corresponding to the internal reference gene β-Actin, and a set of primer probe for non-HLA-B*15:02 genes are designed to detect whether a DNA sample contains an HLA-B*15:02 gene and whether a sample is homozygous or heterozygous. Compared with the similar detection methods in the past, the technical scheme in the present disclosure inherits the advantages of high specificity, high throughput, high resolution, low cost, simple and convenient operation, process controllability and the like of the fluorescent PCR, and may detect whether a sample is homozygous or heterozygous.

7 Claims, 4 Drawing Sheets

Specification includes a Sequence Listing.

FIG. 1

FLUORESCENT PCR METHOD FOR DETECTING HLA-B*15:02 ALLELE AND SPECIFIC PRIMER PROBE COMBINATION THEREOF

CROSS REFERENCE TO RELATED APPLICATION

This patent application claims the benefit and priority of Chinese Patent Application NO. 202011431450.8 entitled "Fluorescent PCR method for detecting HLA-B*15:02 allele and specific primer probe combination thereof" filed on Dec. 7, 2020, the entire contents of which are incorporate herein by reference.

REFERENCE TO SEQUENCE LISTING

A computer readable TXT file entitled "Sequence Listing", that was created on May 31, 2023, with a file size of 3336 bytes, contains the sequence listing for this application, has been filed with this application, and is hereby incorporated by reference in its entirety.

TECHNICAL FIELD

The present disclosure relates to a specific primer probe combination for detecting HLA-B*15:02 allele and a detection method.

BACKGROUND ART

Human leukocyte antigen (HLA) is a highly polymorphic alloantigen expressed by major histocompatibility complex (MHC) and is a glycoprotein formed by non-covalent binding of an α heavy chain (glycosylated) and a R light chain.

HLA is divided into class I antigen and class II antigen according to its distribution and function. The essence of HLA-I antigen molecule is the presenting molecule of endogenous antigen, which plays a vital role in human immune response. The specificity of HLA-I antigen depends on the α heavy chain, which is encoded by HLA-A, HLA-B and HLA-C loci. Among them, HLA-B locus is often used as a genetic marker for certain diseases, such as psoriasis, adolescent insulin-dependent diabetes mellitus (IDDM), and so on.

Carbamazepine (CBZ) is a tricyclic anticonvulsant that has been widely used for treating neurological diseases such as epilepsy. Recent studies have shown that the HLA-B*15:02 gene has a strong correlation with the Stevens-Johnson syndrome (SJS) induced by carbamazepine. Clinical statistics show that the frequency of carrying certain HLA locus-related alleles in patients with SJS caused by carbamazepine administration is significantly higher than that in the general population. The HLA-B gene is listed as a biomarker of carbamazepine in the Table of Pharmacogenomic Biomarkers in Drug Labeling by FDA (US Food and Drug Administration), and the signs such as warnings and preventive measures are printed on the packaging box.

At present, the main HLA genotype detection methods include PCR-sequence specific primer (PCR-SSP), PCR-sequencing based typing (PCR-SBT) and Fluorescent Quantitative PCR (Real time-PCR). Among them, PCR-SSP and PCR-SBT methods have the disadvantages of cumbersome operation, long time consumption, and high cost. However, RT-PCR has become the main method for detecting HLA-B*15:02 because of its advantages of high throughput, rapid and simple operation, no pollution, and real-time monitoring the reaction process.

The existing kits for detecting HLA-B*15:02 based on the RT-PCR method mainly identify whether a sample is positive for HLA-B*15:02 according to the principle of simultaneous detection of multiple HLA-B gene loci. For example, the Chinese Patent NO. CN2015102365550 entitled "Multiplex real-time fluorescent PCR method for detecting HLA-B*15:02 alleles" provides a TaqMan probe detection method for qualitatively identifying HLA-B*15:02 genes, in its scheme, multiple SNP loci are simultaneously used to identify whether a sample is positive for HLA-B*15:02, and the method has the following shortcomings:

1. multiple amplification products are involved, and the method is highly complex;
2. the final specificity is limited to database updates and needs to be improved;
3. unable to distinguish homozygote from heterozygote.

Therefore, the inventors consider that if a few gene loci with high specificity are used for detecting HLA-B*15:02, the detection efficiency and quality will be greatly improved.

SUMMARY OF THE INVENTION

The objective of the present disclosure is to provide an efficient and accurate method for detecting HLA-B*15:02 genotype.

In order to achieve the above object, the present disclosure provides a method for detecting HLA-B*15:02 genotype at a single gene locus. The research ideas are as follows:

First, a total of 1449 known HLA-B genotypes are obtained and HLA-B*15:02:01:01 is used as the reference gene sequence for sequence alignment with all other alleles. By analyzing the comparison results, it is known that about 3,400 base loci of the gene are specific to HLA-B*15:02, i.e., each locus can distinguish the HLA-B*15:02 genotype from the non-HLA-B*15:02 genotype. It is found that the rs144012689 (T/A), a SNP locus located on the fifth intron, can distinguish the HLA-B*15:02 genotype from the other genotypes in 99.7%(1446/1449) of all HLA-B alleles, and combinations with other loci can not achieve high specificity. The three indistinguishable genotypes are B015:438, B015:454N, B015:491, and the gene frequencies of the three genes are extremely low or not found through searching. Therefore, we use the SNP locus as a specific locus for this method.

Based on this, the inventor further conducts analysis and experiments, and obtains the following technical schemes:

A specific primer probe combination for HLA-B*15:02 allele, including:

```
HLA-B*15:02 allele-specific forward
primer Fm:
                                  (SEQ ID NO: 1)
5'-CCTCATTACTGGGAAGCAGCATCAT-3';

non-HLA-B*15:02 allele-specific forward
primer Fn1:
                                  (SEQ ID NO: 2)
5'-CCTCATTACTGGGAAGCAGCATCAA-3';

non-HLA-B*15:02 allele-specific forward
primer Fn2:
                                  (SEQ ID NO: 3)
5'-CCTCATTACTGGGAAGCAGCATGAA-3';
```

```
reverse primerR:
                                    (SEQ ID NO: 4)
5'-CCACAACCATCAAGGCGATACATCT-3';

probeP:
                                    (SEQ ID NO: 5)
5'-ROX-ACGCAGCCTGGGACCCTGTGTGCCAGCA-BHQ1-3';
``` wherein ROX is a fluorescent group, and Carboxy-X-RhoDamine may be selected; BHQ1 is a quenching group, and Black Hole Quencher-1 may be selected.

The 5' end of the above probe is modified as a fluorescent group, and specifically, other fluorescent groups may be replaced as long as there is no overlapping absorption peak with the probe-modified fluorescent group designed for the internal reference gene. Based on the well-known fluorescent PCR method, the corresponding alternatives for such fluorophores should also be considered within the scope of the present invention.

Optionally, the specific primer probe combination further includes specific primers and probes designed for the internal reference gene β-Actin, which are specifically as follows:

```
forward primer ACTB-F:
                                    (SEQ ID NO: 6)
5'-CTCTCTGACTAGGTGTCTAAGACA-3';

reverse primer ACTB-R:
                                    (SEQ ID NO: 7)
5'-GAGTCTGTTCAGACCTACTGTG-3';

probe ACTB-P:
                                    (SEQ ID NO: 8)
5'-FAM-AGGTACTAACACTGGCTCGTGTGAC-BHQ1-3';
``` wherein, FAM is a fluorescent group, and 6-carboxyfluorescein may be selected, BHQ1 is a quenching group, and Black Hole Quencher-1 may be selected.

The 5' end of the above probe is modified as a fluorescent group. Similarly, other fluorescent groups may also be replaced as long as there is no overlapping absorption peak with the fluorescent group of the above probe P.

The present disclosure also provides that the above-mentioned specific primer probe combination may be used for preparing a detection tool for detecting the HLA-B*15:02 allele by fluorescent PCR reaction.

The common forms of the above detection tools include kits, chips, and the like.

For example, a kit for detecting the HLA-B*15:02 allele by fluorescent PCR reaction, especially a kit containing the above-mentioned specific primer probe combination.

The present disclosure also provides a TaqMan probe real-time fluorescent PCR method for detecting the HLA-B*15:02 allele, which is used for non-disease diagnosis purposes, and includes the following steps:
1) acquiring a genomic DNA of a sample to be tested;
2) adding the genomic DNA of the sample to be tested, a specific prim probe combination and PCR related reaction reagents in a HLA-B*15:02 alleles positive reaction system and a HLA-B*15:02 alleles negative reaction system according to a ratio respectively;
3) detecting the reaction systems by fluorescence PCR, collecting fluorescence signals of the ROX and FAM fluorescence channels;
4) analyzing and judging the conditions of the HLA-B*15:02 allele carried by the sample to be tested by the fluorescence signal results.

In some embodiments, the PCR related reaction reagents include dNTP, Taq DNA polymerase, PCR reaction buffer, and double distilled water for supplementing the system.

In some embodiments, the reaction system is 20 μL, including:

Tube 1: 4 μL of 5×buffer, 2 μL of 10×buffer, 2 μL of dNTP, 0.4 μL of forward primer Fm, 0.4 μL of reverse primer R, 0.2 μL of probe P, 0.2 μL of internal reference forward primer, 0.2 μL of internal reference reverse primer, 0.1 μL of internal reference probe, 0.2 μL of Taq DNA polymerase, and 2 μL of genomic DNA of the sample to be tested, the volume is made up to 20 μL with double distilled water.

Tube 2: 4 μL of 5×buffer, 2 μL of 10×buffer, 2 μL of dNTP, 0.2 μL of forward primer Fn1, 0.2 μL of forward primer Fn2, 0.4 μL of reverse primer R, 0.2 μL of probe P, 0.2 μL of internal reference forward primer, 0.2 μL of internal reference reverse primer, 0.1 μL of internal reference probe, 0.2 μL of Taq DNA polymerase, and 2 μL of genomic DNA of the sample to be tested, the volume is made up to 20 μL with double distilled water.

Among them, 5×buffer, 10×buffer and Taq DNA polymerase are from Hotstart HiTaq DNA Polymerase, a product of Fapon Biotech Inc.

In some embodiments, the PCR amplification program is:
Hold Stage: 50° C. 2 min; 95° C. 10 min;
PCR Stage: 35 cycles in total: 95° C. for 15 s; 60° C. for 35 s.

In some embodiments, the basis for judging the final detection result is as follows:

Specific primers and probes of a target gene and an internal reference gene are amplified in a double tube on a fluorescent PCR instrument, and the fluorescence is collected through corresponding channels; the internal reference gene is used as the quality control, and a fluorescence amplification curve must be displayed, otherwise the result is regarded as invalid; on the premise of successful amplification of the internal reference gene:
(a) if there is no amplification curve for HLA-B*15:02 allele positivity while there is an amplification curve for HLA-B*15:02 allele negativity, the sample is homozygous for HLA-B*15:02 allele negativity;
(b) if there is a fluorescent signal corresponding to the forward primer for the HLA-B*15:02 positive allele, the sample is HLA-B*15:02 positive; on the basis of HLA-B*15:02 positivity, the sample is an HLA-B*15:02 positive heterozygote if there is an amplification curve for HLA-B*15:02 allele negativity, otherwise, the sample is an HLA-B*15:02 positive homozygote.

In the present disclosure, a set of primers and probes are designed based on an HLA-B*15:02 specific SNP gene locus by using TaqMan probe technology, combining another set of primers and probes corresponding to the internal reference gene β-Actin, whether a DNA sample contains an HLA-B*15:02 gene is analyzed by a fluorescence signal result obtained by fluorescence quantitative PCR reaction. On this basis, a set of primer probes for non-HLA-B*15:02 genes are designed to detect whether a sample is homozygous or heterozygous. Compared with the similar detection methods in the past, the technical scheme in the present disclosure inherits the advantages of high specificity, high throughput, high resolution, low cost, simple and convenient operation, process controllability and the like of the fluorescent PCR, and additionally adds the detection function for heterozygotes and homozygotes. Specifically, it has the following beneficial effects:

1. High Throughput, High Efficiency

By using the classical TaqMan probe fluorescent quantitative PCR technology, the corresponding target gene may be quickly and accurately detected by designing primers and probes specifically combined with the target gene, and the experimental operation is simple, and the experimental result may be obtained by PCR reaction in less than two hours.

2. Strong Specificity and High Sensitivity

On the basis of TaqMan probe technology, additional mismatches are artificially introduced by using the ARMS principle, which greatly reduces the probability of non-specific combination of primers and probes with a DNA template, and improves the reliability of detection.

3. Low Cost, Low Threshold

Compared with first-generation sequencing, the method in the present disclosure may complete the detection only by fluorescent quantitative PCR, and the only equipment required is a fluorescent quantitative PCR instrument, so that the method is more economical and practical compared with the traditional methods.

4. High Safety and Pollution Free

Reagents used in the reaction are harmless to human bodies, the reaction products will not cause great negative impact on the environment, and the method has the features of environmental protection and safety.

5. This Method May Detect Heterozygosity and Homozygosity of Samples.

BRIEF DESCRIPTION OF THE DRAWINGS

FIG. 1 shows the partial alignment results by sequence alignment of HLA-B*15:02 as a reference gene with other HLA-B alleles; wherein the nucleotide sequence fragment of B*15:02:01:01 is set forth in SEQ ID NO: 9; the nucleotide sequence fragment of B*07:02:01:01 is set forth in SEQ ID NO: 10; the nucleotide sequence fragment of B*07:02:01:02 is set forth in SEQ ID NO: 11; the nucleotide sequence fragment of B*07:02:01:03 is set forth in SEQ ID NO: 12; the nucleotide sequence fragment of B*07:02:01:04 is set forth in SEQ ID NO: 13.

DETAILED DESCRIPTION OF THE EMBODIMENTS

Figure 2:
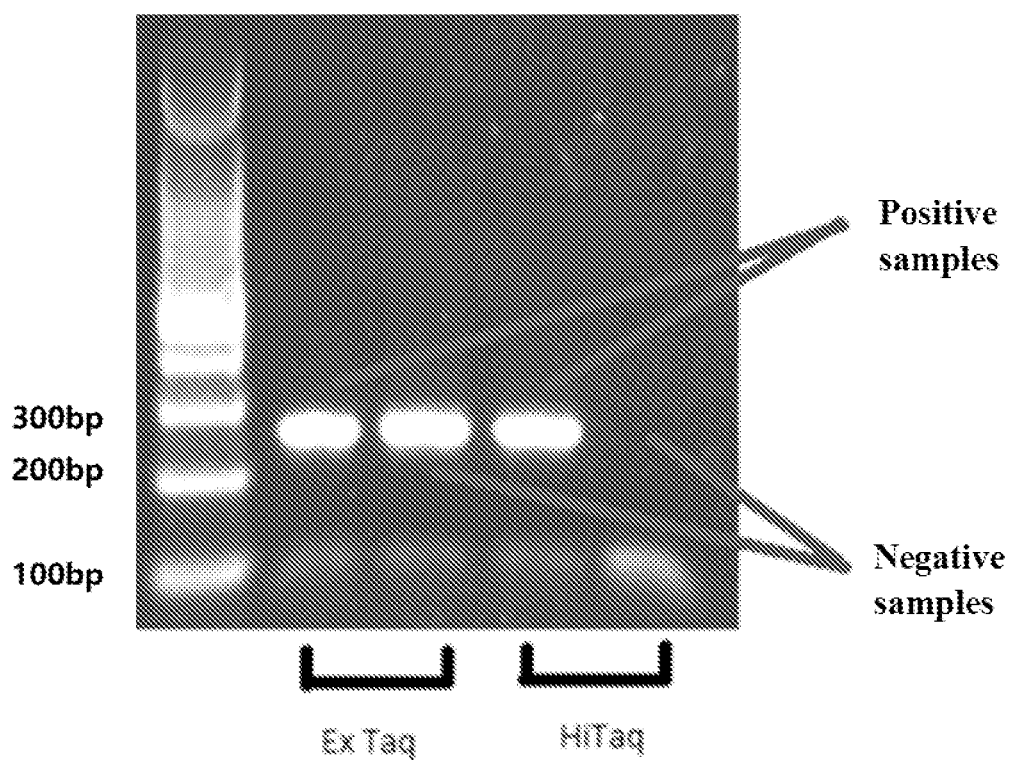
FIG. 2 shows the results of a control experiment using two polymerases.

The development process of the present disclosure is briefly described below, and the scheme of the present disclosure is further described in detail by examples.

It should be recognized that the following description of the development process of the present disclosure only selects part of the salient points, intending to show that the final scheme of the present disclosure is not available to those skilled in the art from a simple and limited experiments.

Figure 1:
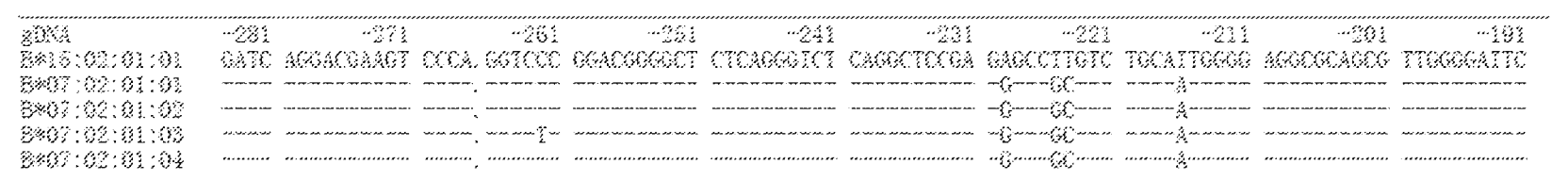

The HLA-B allele sequences are obtained from the Immuno Polymorphism Database (IPD) of EMBL-EBI, HLA-B*15:02 is used as the reference gene for sequence alignment with other HLA-B alleles, and the alignment results are obtained, some results are shown in FIG. 1. In which, each row represents each HLA-B allele, and each column represents the comparison of each allele with the HLA-B:15*02 gene at each locus, "-" represents a match, and "." represents a vacancy, and the bases "A", "T", "C" and "G" represent the corresponding bases which are different from the HLA-B:15*02 gene at the locus and are marked. For example, the base of HLA-B*07:02:01:03 at −262 is T, while the base of HLA-B:15*02 is C at this locus, which can be used as the basis for finding specific loci.

According to experience, simultaneous differentiation of the HLA-B:15*02 gene with as many other genes as possible is achieved by multiple specific loci simultaneous detection. Therefore, the data are processed, the result of sequence alignment is first converted into a matrix, where the vacancy "." and the same base "-" are represented by 0, indicating that the locus could not identify HLA-B:15*02 and the corresponding allele; the results of mismatching, that is, "A", "T", "C" and "G", are represented by 1, indicating that this locus may identify HLA-B:15*02 and the corresponding allele, i.e., this locus is the specific locus for identifying HLA-B:15*02 and the corresponding allele.

TABLE 1

| — | — | A |
|---|---|---|
| G | — | — |
| G | ↓ | — |
| 0 | 0 | 1 |
| 1 | 0 | 0 |
| 1 | 0 | 0 |

As shown in Table 1, the locus represented in the first column may distinguish the HLA-B:15*02 gene from the alleles represented in the second row and the third row, and the locus represented in the third column may distinguish the HLA-B:15*02 gene from the alleles represented in the first row, then detecting the loci represented in the first column and the third column at the same time may distinguish the HLA-B:15*02 gene from the three alleles simultaneously. According to this idea, the comparison results are converted into a matrix containing only "1" and "0", and the number of non-zero elements in each column vector is the number of alleles that can be distinguished at that locus. As shown in the above table, the number of non-zero elements in the first column is 2, and the number of non-zero elements in the third column is 1, which indicates that the number of alleles that may be distinguished at the corresponding loci in the first column and the third column are 2 and 1. On this basis, the number of non-zero elements in the obtained result by adding multiple column vectors is the number of alleles that may be distinguished by simultaneous detection of multiple loci, as shown in the above table, [0,1,1] plus [1,0,0] equals to [1,1,1], wherein the number of non-zero elements is 3, which means that simultaneous detection of the corresponding loci in the first column and the third column may simultaneously distinguish the HLA-B:15*02 gene from three alleles.

According to the above method, the whole sequence is screened for specific locus combination, and the optimal result is the combination of rs1050388, rs151341118, rs1050692, rs41540133 and rs144012689. The number of alleles that could be distinguished among the 3191 HLA-B alleles is 3191, and the degree of distinction is 100%. Each locus in the combination is analyzed, the number of alleles that could be distinguished from rs144012689 is 3187, and the number of alleles that could be distinguished from the remaining four specific loci is 1, in which, the distinguishable allele for rs1050388 is HLA-B*15:13:01, the distinguishable allele for rs151341118 is HLA-B*15:438, the distinguishable allele for rs1050692 is HLA-B*15:454N, the distinguishable allele for rs41540133 is HLA-B*15:491. The four alleles are investigated in the Allele Frequency Net Database (AFND) and found that the gene frequencies in China are all below 0.01%, and thus specific primer probes only for rs144012689 are designed.

Analyzing the forward and reverse sequences of rs144012689, another specific locus rs2596496 is found at two bases forward. Therefore, rs144012689 may be used as the 3' end of the forward primer, and the combination of multiple primers and single probe combined with the Amplification Refractory Mutation System (ARMS) method may not only identify the HLA-B:15*02 gene, but also determine the heterozygosity of the HLA-B:15*02 gene in the sample through the heterozygosity of rs144012689.

The reagents frequently used in the past are selected for experiments, and it is found that the previously used Takara-Premix Ex Taq kit has the disadvantages of high amplification efficiency and poor specificity, and severe non-specific amplification would occur. Therefore, in combination with the product investigation on related polymerases, HotstartHiTaq DNA Polymerase is finally used. Two enzymes are used to conduct control experiments on negative and positive samples, and the results are shown in FIG. 2. The first two columns are the results of using Takara Premix Ex Taq, the last two columns are the results of using HotstartHiTaq DNA Polymerase, columns 1 and 3 are for positive samples, and columns 2 and 4 are for negative samples. In the results of this experiment, a false-positive result is obtained for Takara Premix Ex Taq, while the results for HotstartHiTaq DNA Polymerase are accurate.

Figure 3:
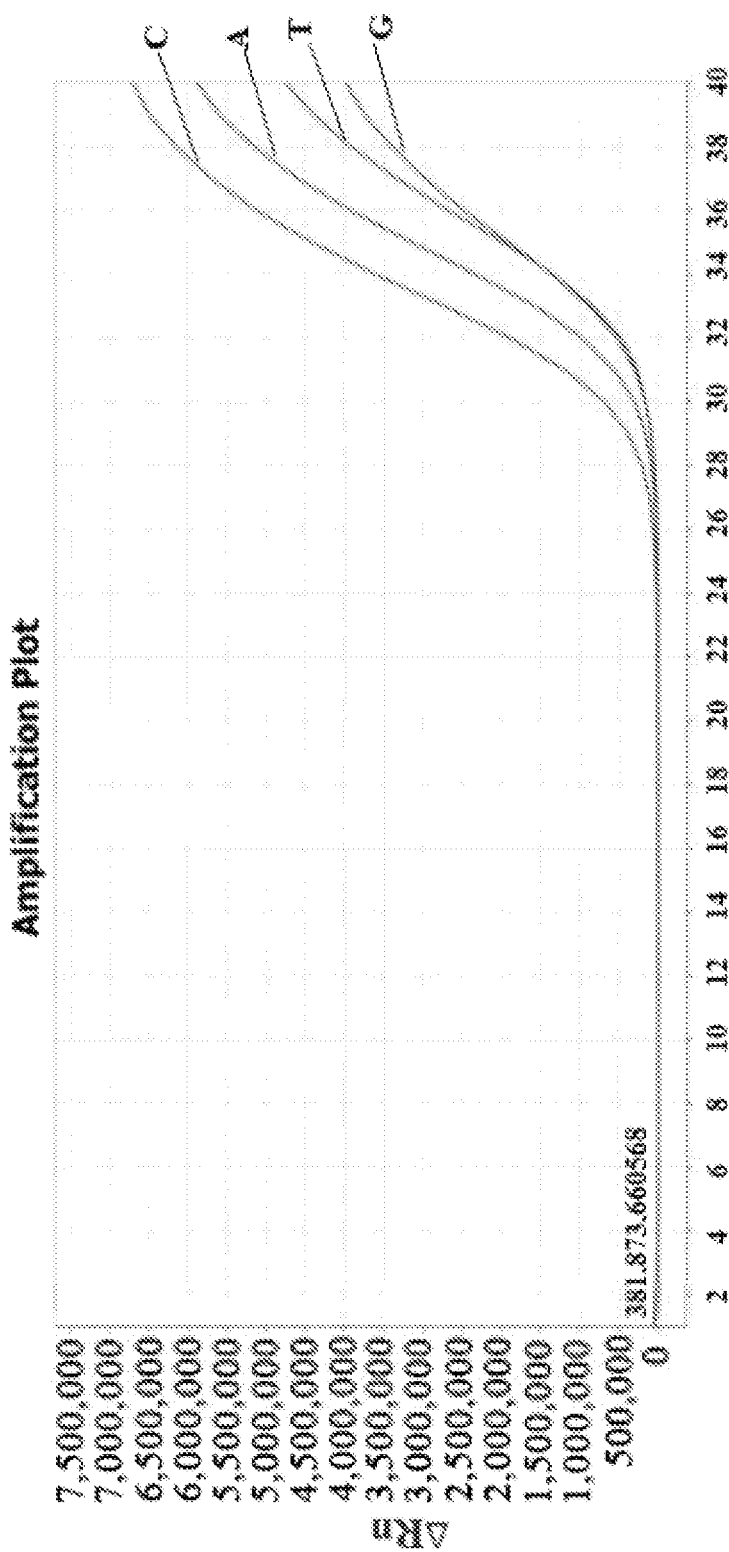
FIG. 3 is a schematic diagram showing the results of introducing a different mismatched base to one base forward of the rs144012689 locus.

Based on the Amplification Referential Mutation System (ARMS) method, a mismatched base is artificially introduced into one base forward of the rs144012689 locus, while the correctly matched base is C, therefore the primers with three bases (A, G and T) at the corresponding loci are designed and experimented, and the results are shown in FIG. 3. In which, according to the CT value from small to large, the corresponding bases at the ARMS locus are C, A, G and T. Because the C\G and C\T mismatches are too strong, resulting in an excessive decrease in amplification efficiency, which could result in a false negative result, the final ARMS mismatch base is determined to be A.

An example of the present disclosure will be described below.

1. Preparation of Samples

DNA was extracted from peripheral blood samples using a QIAamp DNA Mini Blood Kit (Qiagen, Germany).

2. Design of Primers

The specific primers and probes for the HLA-B*15:02 gene were as follows:

```
forward primer Fm:
                                          (SEQ ID NO: 1)
5'-CCTCATTACTGGGAAGCAGCATCAT-3';

reverse primer R:
                                          (SEQ ID NO: 4)
5'-CCACAACCATCAAGGCGATACATCT-3';

Probe P:
                                          (SEQ ID NO: 5)
5'-ROX-ACGCAGCCTGGGACCCTGTGTGCCAGCA-BHQ1-3'.
```

The specific primers and probes for the non-HLA-B*15:02 genes were as follows:

```
forward primer Fn1:
                                          (SEQ ID NO: 2)
5'-CCTCATTACTGGGAAGCAGCATCAA-3';

forward primer Fn2:
                                          (SEQ ID NO: 3)
5'-CCTCATTACTGGGAAGCAGCATGAA-3';

reverse primer R:
                                          (SEQ ID NO: 4)
5'-CCACAACCATCAAGGCGATACATCT-3';

Probe P:
                                          (SEQ ID NO: 5)
5'-ROX-ACGCAGCCTGGGACCCTGTGTGCCAGCA-BHQ1-3';
``` wherein ROX was Carboxy-X-RhoDamine; BHQ1 was Black Hole Quencher-1.

The primers and probes for the internal reference gene ACTB were as follows:

```
forward primer ACTB-F:
                                          (SEQ ID NO: 6)
5'-CTCTCTGACTAGGTGTCTAAGACA-3';

reverse primer ACTB-R:
                                          (SEQ ID NO: 7)
5'-GAGTCTGTTCAGACCTACTGTG-3';

Probe ACTB-P:
                                          (SEQ ID NO: 8)
5'-FAM-AGGTACTAACACTGGCTCGTGTGAC-BHQ1-3';
``` wherein FAM was 6-carboxy-fluorescein, and BHQ1 was Black Hole Quencher-1.

3. Sample Detection

The reaction system was 20 μL, including: Tube 1: 4 μL of 5×buffer, 2 μL of 10×buffer, 2 μL of dNTP, 0.4 μL of forward primer Fm, 0.4 μL of reverse primer R, 0.2 μL of probe P, 0.2 μL of internal reference forward primer, 0.2 μL of internal reference reverse primer, 0.1 μL of internal reference probe, 0.2 μL of Taq DNA polymerase, and 2 μL of genomic DNA of the sample to be tested, the volume is made up to 20 μL with double distilled water.

Tube 2: 4 μL of 5×buffer, 2 μL of 10×buffer, 2 μL of dNTP, 0.2 μL of forward primer Fn1, 0.2 μL of forward primer Fn2, 0.4 μL of reverse primer R, 0.2 μL of probe P, 0.2 μL of internal reference forward primer, 0.2 μL of internal reference reverse primer, 0.1 μL of internal reference probe, 0.2 μL of Taq DNA polymerase, and 2 μL of genomic DNA of the sample to be tested, the volume is made up to 20 μL with double distilled water.

The PCR amplification program was:
Hold Stage: 50° C. 2 min; 95° C. 10 min;
PCT Stage (35 cycles) 95° C. for 15 s; 60° C. for 35 s.

4. Analysis of Results

The internal reference gene was used as the quality control, and a fluorescence amplification curve must be displayed, otherwise the result was regarded as invalid; on the premise of successful amplification of the internal reference gene, if there was no amplification curve for HLA-B*15:02 allele positivity while there was an amplification curve for HLA-B*15:02 allele negativity, the sample was homozygous for HLA-B*15:02 allele negativity. If there was a fluorescent signal corresponding to the forward primer for the HLA-B*15:02 positive allele, the sample was HLA-B*15:02 positive; on the basis of HLA-B*15:02 positivity, the sample was an HLA-B*15:02 positive heterozygote if there was an amplification curve for HLA-B*15:02 allele negativity, otherwise, the sample was an HLA-B*15:02 positive homozygote.

5. Experimental Results

Figure 4:
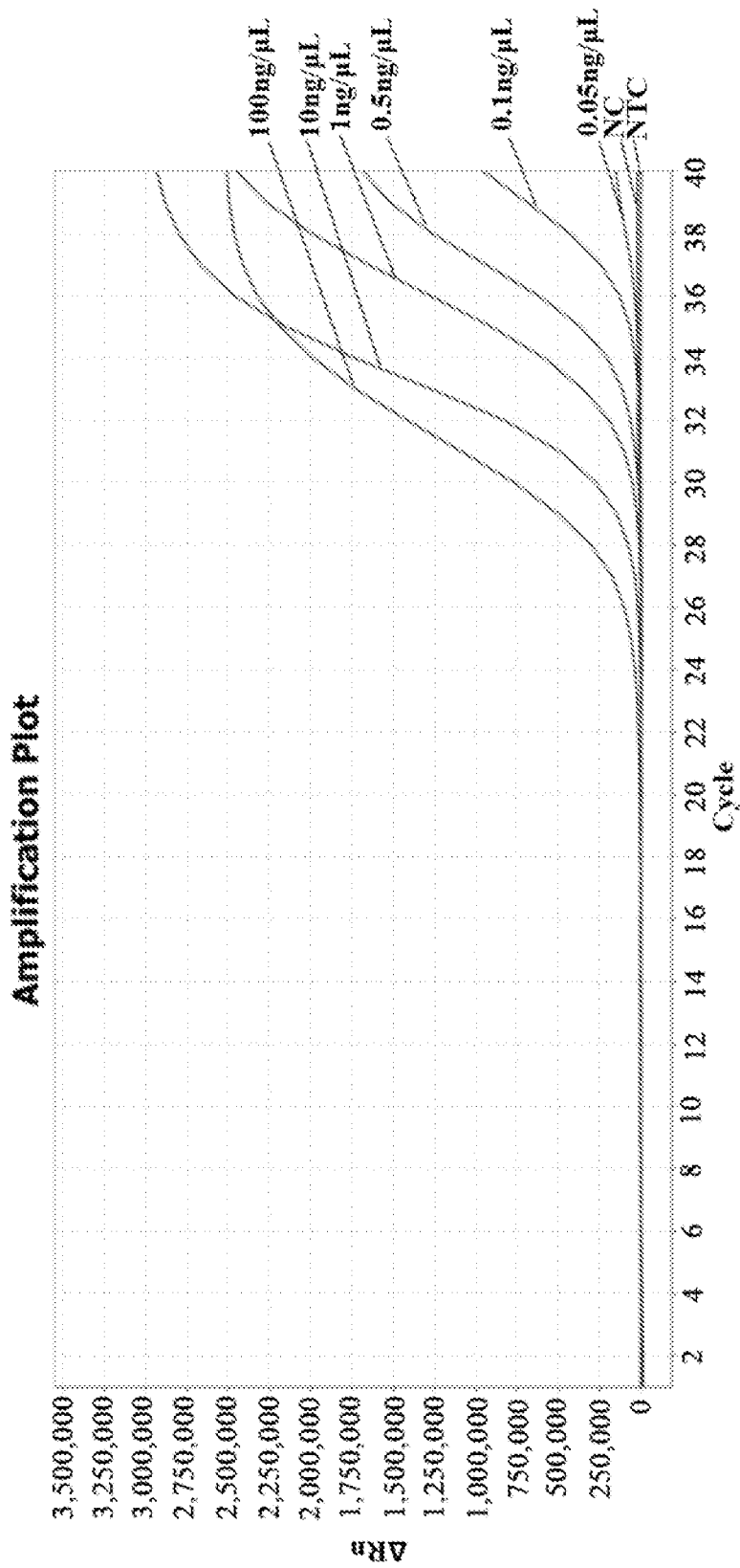
FIG. 4 is a schematic diagram of dilution results of a positive standard product in an embodiment of the present disclosure.

The ROX channel signal of the positive standard dilution result was shown in FIG. 4, from which a recommended sample concentration was 10 ng/μL.

Verification experiment: 100 random samples were amplified, and the results were compared with those of SBT sequencing (Beijing BoFurui Medical Laboratory Co., Ltd.) to determine the accuracy and sensitivity of the method. The results were shown in Table 2, and the accuracy and sensitivity of this method were both 100%.

TABLE 2

Results compared with SBT sequencing method

|  |  | SBT sequencing | | | |
|---|---|---|---|---|---|
|  |  | Positive homozygosity | Positive heterozygosity | Negative | Total |
| PCR results | Positive homozygosity | 1 | 0 | 0 | 1 |
|  | Positive heterozygosity | 0 | 10 | 0 | 10 |
|  | Negative | 0 | 0 | 89 | 89 |
|  | Total | 1 | 10 | 89 | 100 |

The method for detecting the HLA-B*15:02 genotype by single gene locus provided in the example has the advantages of high efficiency and accuracy, good specificity and simple operation process, which is beneficial to guiding the safe medication of carbamazepine on the basis of HLA-B*15:02 allele typing.

In addition, base on the above specific primer probe combinations, by using the existing technical means, detection tools, such as a kit and a chip, for detecting the HLA-B*15:02 allele based on the fluorescent PCR reaction may be prepared accordingly.

What is claimed is:

1. A specific primer probe combination for HLA-B*15:02 allele, comprising:
    HLA-B*15:02 allele-specific forward primer Fm, the nucleotide sequence of Fm is set forth in SEQ ID NO: 1;
    non-HLA-B*15:02 allele-specific forward primer Fn1, the nucleotide sequence of Fn1 is set forth in SEQ ID NO: 2;
    non-HLA-B*15:02 allele-specific forward primer Fn2, the nucleotide sequence of Fn2 is set forth in SEQ ID NO: 3;
    reverse primer R, the nucleotide sequence of R is set forth in SEQ ID NO: 4; and
    probe P: 5'-Carboxy-X-Rhodamine-ACGCAGCCTGGGACCCTGTGTGCCAGCA quenching group-3', the nucleotide sequence between Carboxy-X-Rhodamine and the quenching group is set forth in SEQ ID NO: 5;
wherein Carboxy-X-Rhodamine is a fluorescent group, and the quenching group has a chemical structure of

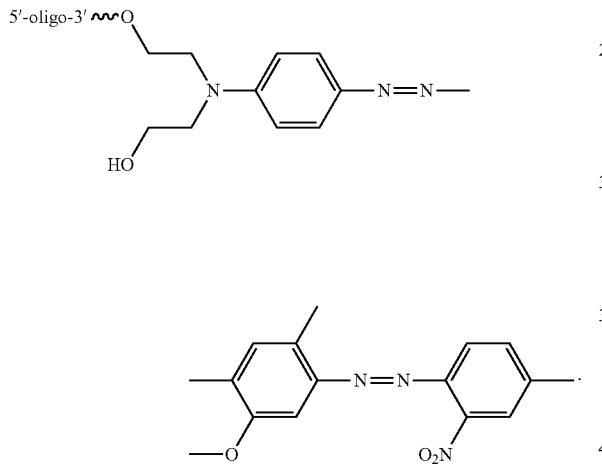

2. The specific primer probe combination according to claim 1, further comprising specific primers and probes designed for an internal reference gene β-Actin, which are as follows:
    forward primer ACTB-F, the nucleotide sequence of ACTB-F is set forth in SEQ ID NO: 6;
    reverse primer ACTB-R, the nucleotide sequence of ACTB-R is set forth in SEQ ID NO: 7; and
    probe ACTB-P: 5'-6-carboxy-fluoroscein-AGGTACTAACACTGGCTCGTGTGAC quenching group-3', the nucleotide sequence of between 6-carboxy-fluorescein and quenching group is set forth in SEQ ID NO: 8;
wherein 6-carboxy-fluorescein is a fluorescent group, and the quenching group has a chemical structure of

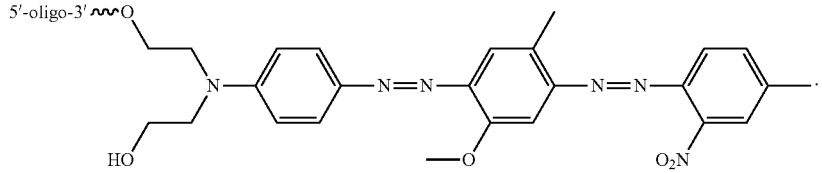

3. A real-time fluorescent PCR method for detecting HLA-B*15:02 allele for non-disease diagnostic purposes, comprising the following steps:
    1) Acquiring the genomic DNA of a sample to be tested;
    2) Adding the genomic DNA of the sample to be tested, a specific primer probe combination according to claim 1 and PCR reagents in a HLA-B*15:02 alleles positive reaction system and a HLA-B*15:02 alleles negative reaction system respectively;
    3) Detecting the reaction systems by fluorescence PCR, collecting fluorescence signal of the Carboxy-X-Rhodamine fluorescence channel; and
    4) judging the conditions of the HLA-B*15:02 allele carried by the sample to be tested by the fluorescence signal results.

4. The method according to claim 3, wherein the PCR reagents comprises dNTP, Taq DNA polymerase, PCR reaction buffer, and double distilled water.

5. The method according to claim 4, wherein the PCR amplification program is:
    Hold Stage: 50° C. 2 min; 95° C. 10 min;
    PCR Stage: 35 cycles in total: 95° C. for 15 s; 60° C. for 35 s.

6. The method according to claim 4, wherein a basis for judging the final detection result is as follows:
    specific primers and probes of a target gene and an internal reference gene are amplified in two separate reaction tubes on a fluorescent PCR instrument, and the fluorescence is collected through corresponding channels; the internal reference gene is used as the quality control, and a fluorescence amplification curve must be displayed, otherwise the result is regarded as invalid; on the premise of successful amplification of the internal reference gene:
        if there is no amplification curve for the HLA-B*15:02 alleles positive reaction system while there is an amplification curve for the HLA-B*15:02 alleles negative reaction system, the sample is homozygous for HLA-B*15:02 allele negativity;
        if there is a fluorescent signal corresponding to the forward primer for the HLA-B*15:02 positive allele, the sample is HLA-B*15:02 positive; on the basis of HLA-B*15:02 positivity, the sample is an HLA-B*15:02 positive heterozygote if there is an amplification curve for HLA-B*15:02 allele negativity, otherwise, the sample is an HLA-B*15:02 positive homozygote.

7. A real-time fluorescent PCR method for detecting HLA-B*15:02 allele for non-disease diagnostic purposes, comprising the following steps:
    1) Acquiring the genomic DNA of a sample to be tested;
    2) Adding the genomic DNA of the sample to be tested, a specific primer probe combination according to claim 2 and PCR reagents in a HLA-B*15:02 alleles positive reaction system and a HLA-B*15:02 alleles negative reaction system respectively;

3) Detecting the reaction system by fluorescence PCR, collecting fluorescence signal of the 6-carboxy-fluorescein fluorescence channel; and 4) judging the conditions of the HLA-B*15:02 allele carried by the sample to be tested by the fluorescence signal results.

* * * * *

SEQUENCE LISTING

```
<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: forward primer Fm

<400> SEQUENCE: 1
cctcattact gggaagcagc atcat                                            25

<210> SEQ ID NO 2
<211> LENGTH: 25
<212> TYPE: DNA
<213> ORGANISM: Artificial Sequence
<220> FEATURE:
<223> OTHER INFORMATION: forward primer Fn1

<400> SEQUENCE: 2
cctcattact gggaagcagc atcaa                                            25

<210> SEQ ID NO 3
<211> LENGTH: 25
<212> TYPE: DNA
<213> ORGANISM: Artificial Sequence
<220> FEATURE:
<223> OTHER INFORMATION: forward primer Fn2

<400> SEQUENCE: 3
cctcattact gggaagcagc atgaa                                            25

<210> SEQ ID NO 4
<211> LENGTH: 25
<212> TYPE: DNA
<213> ORGANISM: Artificial Sequence
```

```
<220> FEATURE:
<223> OTHER INFORMATION: reverse primer R

<400> SEQUENCE: 4
ccacaaccat caaggcgata catct                                         25

<210> SEQ ID NO 5
<211> LENGTH: 28
<212> TYPE: DNA
<213> ORGANISM: Artificial Sequence
<220> FEATURE:
<223> OTHER INFORMATION: Probe P

<400> SEQUENCE: 5
acgcagcctg ggaccctgtg tgccagca                                      28

<210> SEQ ID NO 6
<211> LENGTH: 24
<212> TYPE: DNA
<213> ORGANISM: Artificial Sequence
<220> FEATURE:
<223> OTHER INFORMATION: forward primer ACTB-F

<400> SEQUENCE: 6
ctctctgact aggtgtctaa gaca                                          24

<210> SEQ ID NO 7
<211> LENGTH: 22
<212> TYPE: DNA
<213> ORGANISM: Artificial Sequence
<220> FEATURE:
<223> OTHER INFORMATION: reverse primer ACTB-R

<400> SEQUENCE: 7
gagtctgttc agacctactg tg                                            22

<210> SEQ ID NO 8
<211> LENGTH: 25
<212> TYPE: DNA
<213> ORGANISM: Artificial Sequence
<220> FEATURE:
<223> OTHER INFORMATION: Probe ACTB-P

<400> SEQUENCE: 8
aggtactaac actggctcgt gtgac                                         25

<210> SEQ ID NO 9
<211> LENGTH: 94
<212> TYPE: DNA
<213> ORGANISM: Artificial Sequence
<220> FEATURE:
<223> OTHER INFORMATION: nucleotide sequence fragment of B*15:02:01:01

<400> SEQUENCE: 9
gatcaggacg aagtcccagg tcccggacgg ggctctcagg gtctcaggct ccgagagcct   60
tgtctgcatt ggggaggcgc agcgttgggg attc                               94
```

```
<210> SEQ ID NO 10
<211> LENGTH: 94
<212> TYPE: DNA
<213> ORGANISM: Artificial Sequence
<220> FEATURE:
<223> OTHER INFORMATION: nucleotide sequence fragment of B*07:02:01:01

<400> SEQUENCE: 10
gatcaggacg aagtcccagg tcccggacgg ggctctcagg gtctcaggct ccgagggccg      60
cgtctgcaat ggggaggcgc agcgttgggg attc                                 94

<210> SEQ ID NO 11
<211> LENGTH: 94
<212> TYPE: DNA
<213> ORGANISM: Artificial Sequence
<220> FEATURE:
<223> OTHER INFORMATION: nucleotide sequence fragment of B*07:02:01:02

<400> SEQUENCE: 11
gatcaggacg aagtcccagg tcccggacgg ggctctcagg gtctcaggct ccgagggccg      60
cgtctgcaat ggggaggcgc agcgttgggg attc                                 94

<210> SEQ ID NO 12
<211> LENGTH: 94
<212> TYPE: DNA
<213> ORGANISM: Artificial Sequence
<220> FEATURE:
<223> OTHER INFORMATION: nucleotide sequence fragment of B*07:02:01:03

<400> SEQUENCE: 12
gatcaggacg aagtcccagg tctcggacgg ggctctcagg gtctcaggct ccgagggccg      60
cgtctgcaat ggggaggcgc agcgttgggg attc                                 94

<210> SEQ ID NO 13
<211> LENGTH: 94
<212> TYPE: DNA
<213> ORGANISM: Artificial Sequence
<220> FEATURE:
<223> OTHER INFORMATION: nucleotide sequence fragment of B*07:02:01:04

<400> SEQUENCE: 13
gatcaggacg aagtcccagg tcccggacgg ggctctcagg gtctcaggct ccgagggccg      60
cgtctgcaat ggggaggcgc agcgttgggg attc                                 94
```